(12) United States Patent
Shaw

(10) Patent No.: US 10,949,970 B2
(45) Date of Patent: Mar. 16, 2021

(54) METHODS AND APPARATUS FOR THE APPLICATION OF MACHINE LEARNING TO RADIOGRAPHIC IMAGES OF ANIMALS

(71) Applicant: SignalPET, LLC, San Diego, CA (US)

(72) Inventor: Neil Gavin Shaw, San Diego, CA (US)

(73) Assignee: SIGNALPET, LLC, San Diego, CA (US)

( * ) Notice: Subject to any disclaimer, the term of this patent is extended or adjusted under 35 U.S.C. 154(b) by 0 days.

(21) Appl. No.: 16/783,578

(22) Filed: Feb. 6, 2020

(65) Prior Publication Data

US 2020/0273166 A1   Aug. 27, 2020

Related U.S. Application Data

(62) Division of application No. 16/578,182, filed on Sep. 20, 2019, now Pat. No. 10,593,041.
(Continued)

(51) Int. Cl.
*G06T 7/00* (2017.01)
*G06N 20/00* (2019.01)
(Continued)

(52) U.S. Cl.
CPC ............ *G06T 7/0012* (2013.01); *G06K 9/627* (2013.01); *G06K 9/6256* (2013.01); *G06N 20/00* (2019.01);
(Continued)

(58) Field of Classification Search
None
See application file for complete search history.

(56) References Cited

U.S. PATENT DOCUMENTS 9,940,711 B2   4/2018   Bregman-Amitai
10,039,513 B2   8/2018   Bregman-Amitai
(Continued)

FOREIGN PATENT DOCUMENTS

WO    WO2018119766    7/2018

OTHER PUBLICATIONS

La Perle, "Machine Learning and Veterinary Pathology: Be Not Afraid!", Veterinary Pathology, vol. 56(4) 506-507, 2019.

*Primary Examiner* — David Perlman
(74) *Attorney, Agent, or Firm* — Garson & Gutierrez, PC

(57) ABSTRACT

Methods and apparatus for the application of machine learning to radiographic images of animals. In one embodiment, the method includes receiving a set of radiographic images captured of an animal, applying one or more transformations to the set of radiographic images to create a modified set, segmenting the modified set using one or more segmentation artificial intelligence engines to create a set of segmented radiographic images, feeding the set of segmented radiographic images to respective ones of a plurality of classification artificial intelligence engines, outputting results from the plurality of classification artificial intelligence engines for the set of segmented radiographic images to an output decision engine, and adding the set of segmented radiographic images and the output results from the plurality of classification artificial intelligence engines to a training set for one or more of the plurality of classification artificial intelligence engines. Computer-readable apparatus and computing systems are also disclosed.

9 Claims, 10 Drawing Sheets

Related U.S. Application Data

(60) Provisional application No. 62/808,604, filed on Feb. 21, 2019.

(51) Int. Cl.
    *G06T 3/00*           (2006.01)
    *G06T 7/11*           (2017.01)
    *G06K 9/62*          (2006.01)
    *G16H 30/20*         (2018.01)
    *G16H 30/40*         (2018.01)

(52) U.S. Cl.
    CPC .............. *G06T 3/0006* (2013.01); *G06T 7/11* (2017.01); *G16H 30/20* (2018.01); *G16H 30/40* (2018.01); *G06T 2207/10116* (2013.01); *G06T 2207/20081* (2013.01); *G06T 2207/30004* (2013.01); *G06T 2207/30168* (2013.01)

(56) References Cited

U.S. PATENT DOCUMENTS

| | | |
|---|---|---|
| 10,111,637 B2 | 10/2018 | Bregman-Amitai |
| 2008/0214907 A1 | 9/2008 | Gutkowicz-Krusin et al. |
| 2010/0070293 A1* | 3/2010 | Brown ............... G06Q 50/22 705/2 |
| 2011/0216180 A1 | 9/2011 | Pasini |
| 2012/0183188 A1* | 7/2012 | Moriya ................ G06T 19/00 382/128 |
| 2013/0004043 A1 | 1/2013 | Ross et al. |
| 2013/0070986 A1 | 3/2013 | Peleg et al. |
| 2015/0363564 A1 | 12/2015 | Lai et al. |
| 2018/0096477 A1 | 4/2018 | Avila |
| 2018/0192944 A1 | 7/2018 | Diener et al. |
| 2018/0242943 A1 | 8/2018 | Bregman-Amitai et al. |
| 2019/0005684 A1 | 1/2019 | DeFauw et al. |
| 2019/0046146 A1 | 2/2019 | Bregman-Amitai et al. |
| 2019/0340753 A1 | 11/2019 | Brestel et al. |
| 2020/0226748 A1* | 7/2020 | Kaufman ............. G06K 9/6292 |

\* cited by examiner

METHODS AND APPARATUS FOR THE APPLICATION OF MACHINE LEARNING TO RADIOGRAPHIC IMAGES OF ANIMALS

PRIORITY

This application is a divisional of, and claims the benefit of priority to, co-owned and co-pending U.S. patent application Ser. No. 16/578,182 filed Sep. 20, 2019 and entitled "Methods and Apparatus for the Application of Machine Learning to Radiographic Images of Animals", which claims the benefit of priority to U.S. Provisional Patent Application Ser. No. 62/808,604 filed Feb. 21, 2019 and entitled "Methods and Apparatus for the Application of Machine Learning to Radiographic Images of Animals", the contents of each of the foregoing being incorporated herein by reference in its entirety.

COPYRIGHT

A portion of the disclosure of this patent document contains material which is subject to copyright or mask work) protection. The (copyright or mask work) owner has no objection to the facsimile reproduction by anyone of the patent document or the patent disclosure, as it appears in the Patent and Trademark Office patent file or records, but otherwise reserves all copyright or mask work) rights whatsoever.

BACKGROUND OF THE DISCLOSURE

1. Technological Field

The present disclosure relates generally to the application of machine learning to biological data received from living beings, and more particularly in one exemplary aspect to the application of machine learning to radiographic images of various animal species including, inter alia, canines, felines, other domesticated and non-domesticated animals, and humans.

2. Field of the Disclosure

The utilization of radiology for the capture of radiological images of various species is a mature technology that is widely deployed in medical centers throughout the world. For example, the use of various medical imaging techniques enables a veterinarian to diagnose and treat a wide variety of maladies thereby improving the animal's quality of life. Despite the numerous benefits associated with radiology generally, numerous deficiencies associated with veterinary radiology exist. For example, the capture of radiological images is a significant stressor for the animal, which can result in the capture of poor-quality radiological images due to, for example, animal movement during image capture. Compounding this deficiency is the need to recapture radiological images when the original capture was of poor-quality (e.g., due to radiology technician error), thereby adding additional stress to the animal. Moreover, qualified radiologists are a limited resource resulting in significant delays between the time of image capture and the subsequent reading of these captured images. These delays can result in additional damage, discomfort and/or death for the animal seeking veterinary treatment. Accordingly, improved methods and apparatus are needed to address these, and other known deficiencies present in the prior art.

SUMMARY

The present disclosure satisfies the foregoing needs by providing, inter alia, methods and apparatus for the application of machine learning to radiological images of animals.

In one aspect, a method of training a plurality of classification artificial intelligence engines for classification of various maladies of an animal is disclosed. In one embodiment, the method includes receiving a set of radiographic images captured of the animal; applying one or more transformations to at least a portion of the set of radiographic images captured of the animal, the applying including one or more of rotating, translating, and normalizing to create a modified set of radiographic images; segmenting the modified set of radiographic images using one or more segmentation artificial intelligence engines to create a set of segmented radiographic images; feeding the set of segmented radiographic images to respective ones of the plurality of classification artificial intelligence engines; outputting results from the plurality of classification artificial intelligence engines for the set of segmented radiographic images to an output decision engine; and adding the set of segmented radiographic images and the output results from the plurality of classification artificial intelligence engines to a training set for one or more of the plurality of classification artificial intelligence engines.

In one variant, subsequent to the applying and prior to the segmenting, the method further includes determining whether any anatomy for the animal has been missed within the modified set of radiographic images using an image quality engine; determining whether any image twisting is present within the modified set of radiographic images using the image quality engine; determining whether burn through has been detected within the modified set of radiographic images using the image quality engine; and when any of the acts of determining by the image quality engine has identified an issue, transmitting a notification of the identified issue to a person responsible for capture of the set of radiographic images.

In another variant, the method further includes applying a training set assistance procedure to the output results, the applying of the training set assistance procedure includes: verifying the output results by a quality control group; subsequent to the verifying, forwarding on the output results to a requesting doctor of veterinary medicine (DVM); receiving clinician verification from the requesting DVM; verifying the clinician verification from the requesting DVM; and if necessary, updating the training set for the one or more of the plurality of classification artificial intelligence engines.

In yet another variant, the method further includes determining that the output results exceed a threshold value for one of the plurality of classification artificial intelligence engines; and removing the training set assistance procedure for the one of the plurality of classification artificial intelligence engines.

In yet another variant, the method further includes determining that the output results do not exceed a threshold value for a second of the plurality of classification artificial intelligence engines; and keeping the training set assistance procedure for the second of the plurality of classification artificial intelligence engines.

In yet another variant, the updating of the training set for the one or more of the plurality of classification artificial intelligence engines further includes removing the set of segmented radiographic images and the output results from the training set for the one or more of the plurality of classification artificial intelligence engines.

In another aspect, a non-transitory computer-readable storage apparatus is disclosed. In one embodiment, the non-transitory computer-readable storage apparatus includes a plurality of instructions, that when executed by a processor apparatus, are configured to: receive a set of radiographic images captured of an animal; apply one or more transformations to at least a portion of the set of radiographic images captured of the animal, the application including one or more of a rotation operation, a translation operation, and a normalization operation to create a modified set of radiographic images; segment the modified set of radiographic images using one or more segmentation artificial intelligence engines to create a set of segmented radiographic images; feed the set of segmented radiographic images to respective ones of the plurality of classification artificial intelligence engines; output results from the plurality of classification artificial intelligence engines for the set of segmented radiographic images to an output decision engine; and add the set of segmented radiographic images and the output results from the plurality of classification artificial intelligence engines to a training set for one or more of the plurality of classification artificial intelligence engines.

In one variant, the plurality of instructions, when executed by the processor apparatus, are further configured to output results from the output decision engine to a graphical user interface (GUI), the GUI including the modified set of radiographic images, a centralized radiographic image from the modified set of radiographic images, and a plurality of classifications.

In another variant, the plurality of instructions, when executed by the processor apparatus, are further configured to receive a first selection for one of the plurality of classifications; and highlight one or more of the modified set of radiographic images that were utilized in assessing the first selected one of the plurality of classifications.

In yet another variant, the plurality of instructions, when executed by the processor apparatus, are further configured to cause display of one of the highlighted one or more of the modified set of radiographic images as the centralized radiographic image.

In yet another variant, the plurality of instructions, when executed by the processor apparatus, are further configured to cause display of a first segmentation outline within the centralized radiographic image, the first segmentation outline representing a first anatomical area of interest utilized in the assessment of the first selected one of the plurality of classifications.

In yet another variant, the plurality of instructions, when executed by the processor apparatus, are further configured to receive a second selection for one of the plurality of classifications, the second selection differing from the first selection; and highlight one or more of the modified set of radiographic images that were utilized in assessing the second selected one of the plurality of classifications.

In yet another variant, the plurality of instructions, when executed by the processor apparatus, are further configured to cause display of a second segmentation outline within the centralized radiographic image, the second segmentation outline differing from the first segmentation outline, the second segmentation outline representing a second anatomical area of interest utilized in the assessment of the second selected one of the plurality of classifications.

In yet another aspect, a system for training a plurality of classification artificial intelligence engines for classification of various maladies of an animal is disclosed. In one embodiment, the system includes an image quality engine which receives as input, biological data as well as one or more quality control parameters; one or more segmentation artificial intelligence engines that are trained using one or more segmentation training sets; one or more classification artificial intelligence engines that are trained using one or more classification training sets; and an output decision engine that receives as input, one or more outputs from the one or more classification artificial intelligence engines.

In one variant, the system is configured to receive a set of radiographic images captured of the animal by the image quality engine; apply, by the image quality engine, one or more transformations to at least a portion of the set of radiographic images captured of the animal, the application including one or more of a rotation operation, a translation operation, and a normalization operation to create a modified set of radiographic images; segment the modified set of radiographic images using the one or more segmentation artificial intelligence engines to create a set of segmented radiographic images; feed the set of segmented radiographic images by the one or more segmentation artificial intelligence engines to respective ones of the one or more classification artificial intelligence engines; output results from the one or more classification artificial intelligence engines for the set of segmented radiographic images to the output decision engine; and add the set of segmented radiographic images and the output results from the one or more classification artificial intelligence engines to the one or more classification training sets.

In another variant, the image quality engine is further configured to determine whether any anatomy for the animal has been missed within the modified set of radiographic images; determine whether any image twisting is present within the modified set of radiographic images; determine whether burn through has been detected within the modified set of radiographic images; and when the image quality engine has identified an issue, the image quality engine is configured to transmit a notification of the identified issue to a person responsible for capture of the set of radiographic images.

In yet another variant, the image quality engine is located proximate to a location where the set of radiographic images have been captured of the animal, the image quality engine being located remote from the one or more classification artificial intelligence engines.

In yet another variant, the image quality engine is configured to not only identify the issue, but facilitate correction of the identified issue.

In yet another variant, the system is further configured to apply a training set assistance procedure to the output results, the application of the training set assistance procedure including verification of the output results by a quality control group; subsequent to the verification, forward on the output results to a requesting doctor of veterinary medicine (DVM); receive clinician verification from the requesting DVM; verify the clinician verification from the requesting DVM; and if necessary, update the training set for the one or more classification training sets.

In yet another variant, the system is further configured to determine that the output results exceed a threshold value for one of the one or more classification artificial intelligence engines; and remove the application training set assistance procedure for the one of the one or more classification artificial intelligence engines.

Other features and advantages of the present disclosure will immediately be recognized by persons of ordinary skill in the art with reference to the attached drawings and detailed description of exemplary implementations as given below.

BRIEF DESCRIPTION OF THE DRAWINGS

The features, objectives, and advantages of the present disclosure will become more apparent from the detailed description set forth below when taken in conjunction with the drawings, wherein:

FIG. 3A is a first exemplary graphical user interface display indicative of classifications and confidence levels for a plurality of animals, in accordance with the principles of the present disclosure.

FIG. 3G is a seventh exemplary graphical user interface indicative of a summary of classifications for a given animal, in accordance with the principles of the present disclosure.

Figure 1:
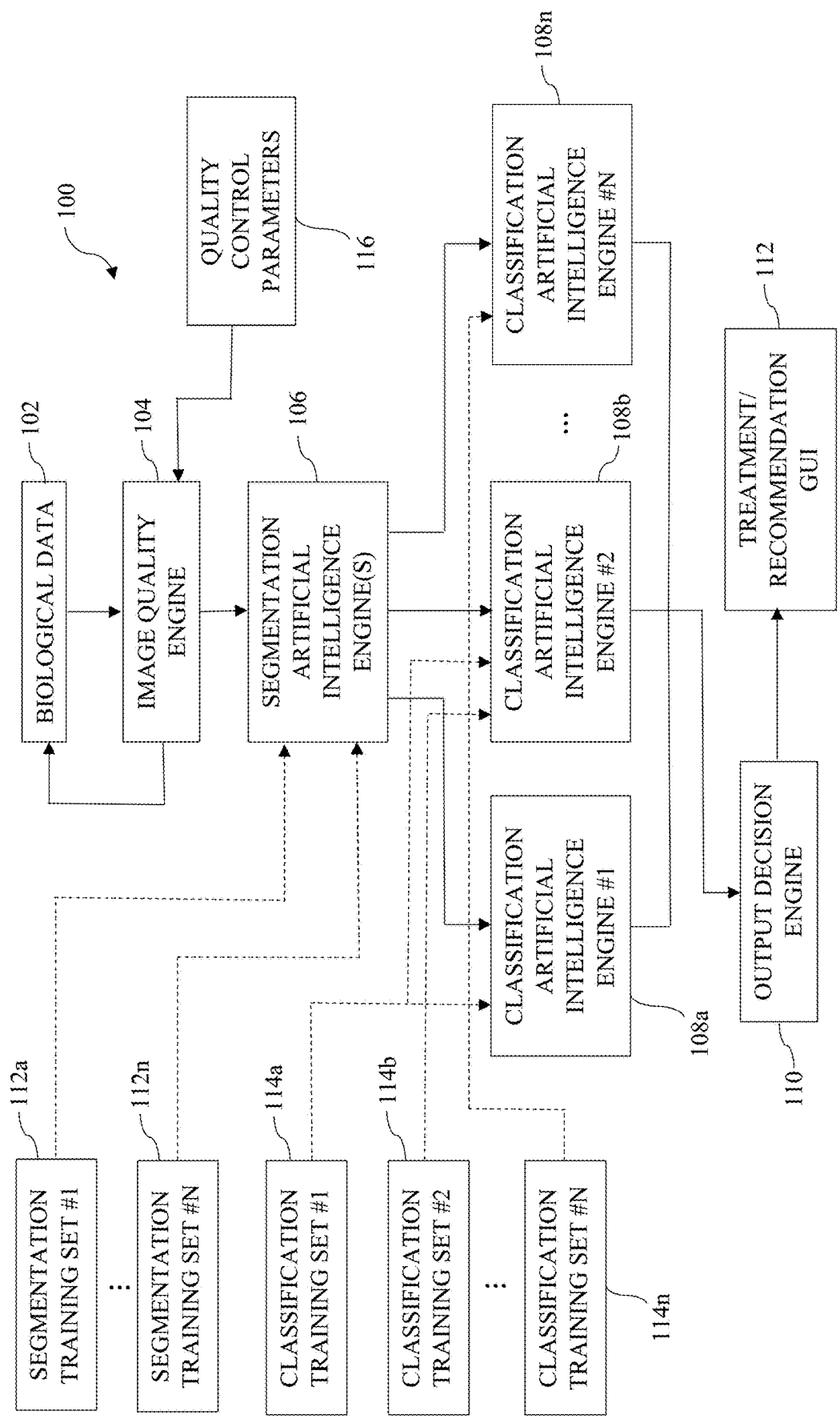
FIG. 1 is a logical block diagram of one exemplary system for classifying conditions of an animal based on biological data, in accordance with the principles of the present disclosure.

All Figures disclosed herein are © Copyright 2019 Westside Veterinary Innovation, LLC. All rights reserved.

DETAILED DESCRIPTION

Overview

Upon establishment (or identification) of basic anatomical criteria, embodiments of the present disclosure contained herein will "learn" about, for example, the radiographic data contained within, for example, captured radiographic images using a database of previously captured radiographic images. This database of captured radiographic images may include, for example, tens of thousands of "smart" labeled images reviewed by qualified expert veterinarian radiologists under quality-controlled processes. These images located in the database may be then used to train machine learning algorithms, which are in turn used on newly received images in order to assist in classification and detection of various maladies. These newly received images may in turn be added to this database of radiographic images in order to further improve the machine learning algorithms. In this fashion, the machine learning algorithms may be allowed to continuously adapt through use (and training) of these machine learning algorithms in order to improve upon its classifications. Through the application of machine learning algorithms to the captured radiographic images, the machine learning algorithms may aid in the identification and classification of various health issue(s) that may be associated with the animal.

In some implementations, the use of the machine learning algorithms involves use of both: (a) a segmentation methodology using one or more segmentation artificial engine(s); and (b) a classification methodology using one or more classification artificial intelligence engine(s). The segmentation methodology may identify specific anatomical area(s) of the animal (e.g., organs, bones, etc.) thereby assisting with the classification, while the classification methodology may classify one or more maladies and/or other identified issues such as, for example, bone fractures, illnesses, disorders, infections, and other common ailments. After execution of the segmentation methodology, the software will execute the classification methodology on these segmented images. The classification methodology may subsequently "grade" the severity of the identified issue using a grading scale that may vary between medically normal to medically abnormal.

Upon execution of the segmentation methodology and/or the classification methodology, the computing system responsible for the classification may transmit a response back to the requesting doctor of veterinarian medicine (DVM). The response may include the graded severity (e.g., strong, medium, or weak, etc.) and may also "highlight" the identified regions within the radiographic images used for the classification with additional margin to ensure the region of interest can be viewed clearly. The response may also include recommended courses of action including, for example, further diagnostics that may be needed in order to support the DVM and the animal and may also include treatment recommendations for the animal that may be based upon, for example, historical success rates. Embodiments disclosed herein create the ability to transfer the radiographic images to clinical applicability and may also be readily applied across a wide swathe of different sizes and anatomies for the animals being examined.

The present disclosure also describes an image quality engine that may be governed by various quality control parameters and/or machine learning algorithms. One disclosed benefit of this image quality engine is to ensure the quality of the radiographic images taken as well as to minimize the stress to the animal while these radiographic images are captured. For example, the image quality engine may also be implemented on-site at the location of the DVM's office, thereby enabling the image quality engine to provide near-real-time feedback to, for example, the technicians responsible for capturing the radiographic images. Additionally, the use of the segmentation and classification methodologies enables animals with more serious maladies to be treated before those animals with less (or no) serious maladies.

EXEMPLARY EMBODIMENTS

Detailed descriptions of the various embodiments and variants of the apparatus and methods of the present disclosure are now provided. It is noted that wherever practicable similar or like reference numbers may be used in the figures and may indicate similar or like functionality. The figures depict embodiments of the disclosed system (or methods) for purposes of illustration only. One skilled in the art will readily recognize from the following description that alternative embodiments of the structures and methods illustrated herein may be employed without necessarily departing from the principles described herein.

While primarily discussed in the context of the application of machine learning to radiographic images such as, for example, two-dimensional (planar) radiological images (e.g., X-rays), it is not necessarily a prerequisite that the application of machine learning to images be confined to two-dimensional images. For example, it is appreciated that variants of the present disclosure may be readily applied to other two-dimensional and three-dimensional imaging techniques such as computed tomography (CT), magnetic resonance imaging (MRI), positron emission tomography (PET), single-photon emission computed tomography (SPECT), ultrasound (sonography) and/or other biological imaging techniques. These and other variants would be readily apparent to one of ordinary skill given the contents of the present disclosure.

Moreover, while primarily discussed in the context of the application of machine learning to biological imaging data, the present disclosure has broader usefulness outside of biological imaging. For example, the techniques described herein may be applied to other biometric data (as discussed subsequently herein) including, for example, vital signs such as pulse, temperature, respiratory rate and the like in order to assist in the identification and treatment of various physiological conditions of an animal. Moreover, other biometric data may be utilized as well, such as audio signals obtained via, for example, a stethoscope (e.g., auscultation of heart sound) and/or use of blood, fecal, and/or other bodily fluid test results. These other biological indicators may be used by the classification and output decision engine(s) in addition to, or alternatively from, the biological imaging techniques described herein to give a more holistic view of the health of an animal.

Exemplary Classification System(s)—

Referring now to FIG. 1, one exemplary system 100 for classifying conditions of an animal based on biological data are shown and described in detail. The functionality of the various modules described herein may be implemented through the use of software executed by one or more processors (or controllers) and/or may be executed via the use of one or more dedicated hardware modules, with the architecture of the system being specifically optimized to execute the artificial intelligence and/or machine learning architectures discussed herein. The computer code (software) disclosed herein is intended to be executed by a computing system that is able to read instructions from a non-transitory computer-readable medium and execute them in one or more processors (or controllers), whether off-the-shelf or custom manufactured. The computing system may be used to execute instructions (e.g., program code or software) for causing the computing system to execute the computer code described herein. In some implementations, the computing system operates as a standalone device or a connected (e.g., networked) device that connects to other computer systems. The computing system may include, for example, a personal computer (PC), a tablet PC, a notebook computer, or other custom device capable of executing instructions (sequential or otherwise) that specify actions to be taken. In some implementations, the computing system may include a server. In a networked deployment, the computing system may operate in the capacity of a server or client in a server-client network environment, or as a peer device in a peer-to-peer (or distributed) network environment. Moreover, a plurality of computing systems may operate to jointly execute instructions to perform any one or more of the methodologies discussed herein.

An exemplary computing system includes one or more processing units (generally processor apparatus). The processor apparatus may include, for example, a central processing unit (CPU), a graphics processing unit (GPU), a digital signal processor (DSP), a controller, a state machine, one or more application specific integrated circuits (ASICs), one or more radio-frequency integrated circuits (RFICs), or any combination of the foregoing. The computing system also includes a main memory. The computing system may include a storage unit. The processor, memory and the storage unit may communicate via a bus.

In addition, the computing system may include a static memory, a display driver (e.g., to drive a plasma display panel (PDP), a liquid crystal display (LCD), a projector, or other types of displays). The computing system may also include input/output devices, e.g., an alphanumeric input device (e.g., touch screen-based keypad or an external input device such as a keyboard), a dimensional (e.g., 2-D or 3-D) control device (e.g., a touch screen or external input device such as a mouse, a trackball, a joystick, a motion sensor, or other pointing instrument), a signal capture/generation device (e.g., a speaker, camera, and/or microphone), and a network interface device, which may also be configured to communicate via the bus.

Embodiments of the computing system corresponding to a client device may include a different configuration than an embodiment of the computing system corresponding to a server. For example, an embodiment corresponding to a server may include a larger storage unit, more memory, and a faster processor but may lack the display driver, input device, and dimensional control device. An embodiment corresponding to a client device (e.g., a personal computer (PC)) may include a smaller storage unit, less memory, and a more power efficient (and slower) processor than its server counterpart(s).

The storage unit includes a non-transitory computer-readable medium on which is stored instructions (e.g., software) embodying any one or more of the methodologies or functions described herein. The instructions may also reside, completely or at least partially, within the main memory or within the processor (e.g., within a processor's cache memory) during execution thereof by the computing system, the main memory and the processor also constituting non-transitory computer-readable media. The instructions may be transmitted or received over a network via the network interface device.

While non-transitory computer-readable medium is shown in an example embodiment to be a single medium, the term "non-transitory computer-readable medium" should be taken to include a single medium or multiple media (e.g., a centralized or distributed database, or associated caches and servers) able to store the instructions. The term "non-transitory computer-readable medium" shall also be taken to include any medium that is capable of storing instructions for execution by the computing system and that cause the computing system to perform, for example, one or more of the methodologies disclosed herein.

Portions of the system 100 of FIG. 1 may be located proximate to one another, while other portions may be located remote from some of the portions. For example, the image quality engine 104 may be located on the premises for the office of the treating DVM, while the segmentation artificial intelligence engine(s) 106, the classification artificial intelligence(s) 108, and the output decision engine 110 may be located remote from the office of the DVM (e.g., within the "cloud"). Moreover, the treatment/recommendation graphical user interface (GUI) 112 may be resident in the office of the DVM as well as in the office of, for example, the assignee of the present disclosure. In other implementations, each of the image quality engine 104, the segmentation artificial intelligence engine(s) 106 and the classification artificial intelligence engine(s) 108 may be located within the premises of the office of the DVM or may be located remote from the office of the DVM (e.g., resident within the cloud, resident within the offices of, for example, the assignee hereof, etc.). These and other variants would be readily apparent to one of ordinary skill given the contents of the present disclosure.

In some implementations, the DVM will install an application on an exemplary computing system located within, for example, the DVM's place of business. This exemplary computing system may access a remote computing system (e.g., a computing system resident in the cloud) that implements some or all of the exemplary functionality disclosed herein. For example, the DVM may capture radiographic images of a subject animal and store these radiographic images on a local computer. These radiographic images may be transmitted over a network (e.g., the Internet) to the remote computing system (e.g., resident within the cloud). If these radiographic image(s) do not already contain metadata that indicates basic criteria such as, for example, (a) species; (b) breed; (c) body positioning; and/or (d) image type, computer code located on the remote computing system may employ machine-learning algorithms (such as those described herein), in order to determine such basic criteria.

The system 100 of FIG. 1 is directed towards the creation of a solution to improve the quality of patient care for animals, improve access to care for animal-owners, and/or enhance the capabilities and assist the treating DVM. Specifically, the system 100 of FIG. 1 described herein applies machine learning to, for example, radiographic images (e.g., digital imaging and communications in medicine (DICOM) images) in order to assist in the identification and classification of various maladies including, inter alia, bone fractures, organ abnormalities, chronic conditions, and/or identification/classification of other useful information typically performed using, for example, biological imaging techniques.

Biological data storage module 102 may receive biological data from a device which captures the biological data. For example, in the context of two-dimensional radiographic imaging (e.g., X-rays), the biological data may be captured by the radiographic imaging machine and transmitted to/received by the biological data storage module 102. The biological data storage module 102 may store other types of biological data in addition to, or alternatively from, the aforementioned two-dimensional radiographic imaging data. For example, three-dimensional imaging data may be received from other types of imaging apparatus, including for example, imaging data obtained from computed tomography (CT), magnetic resonance imaging (MM), positron emission tomography (PET), single-photon emission computed tomography (SPECT), ultrasound (sonography) and/or other biological imaging techniques. The biological data stored within biological data storage module 102 may also include non-imaging data. For example, vital signs such as pulse, temperature, respiratory rate and the like may be stored within the biological data storage module 102. Other types of biological data may be stored as well, such as audio signals obtained via, for example, a stethoscope (e.g., auscultation of heart sound) and/or storage of blood, fecal, and/or other bodily fluid test results. These other biological data may be used in addition to, or alternatively from, the biological imaging data described herein to give a more holistic view of the health of an animal.

In some implementations, the system 100 may include an image quality engine 104 that may be governed by one or more quality control parameters 116. One purpose of the image quality engine 104 may be too quickly notify personnel that the biological data captured may be of insufficient quality in order to properly classify conditions associated with the animal. For example, in the context of captured imaging data, the image quality engine 104 may indicate that a part of the anatomy of the animal has been missed or may indicate that portions of the anatomy important for classification has only partially been captured. The image quality engine 104 may also indicate that the images captured of the animal have been improperly captured (e.g., the animal has not been properly positioned and/or the animal may have moved during image capture). The image quality engine 104 may also indicate that the imaging data may have been captured using less than optimal image capture settings. For example, the image quality engine 104 may detect when a captured image (or portions thereof) has been over-exposed and/or under-exposed, which may be dependent upon, for example, the types of data intended to be captured. For example, a radiographic image that is adequately exposed for soft tissue structures may often be underexposed for bony details, etc.

In some implementations, it may be desirable to implement the image quality engine 104 at the premises of, for example, the DVM in order to facilitate the speed of the indication. For example, capturing radiological images of an animal is oftentimes a significant stressor to the animal undergoing radiological imaging. Accordingly, it may be desirable to minimize the time and/or number of instances in which the animal undergoes radiological imaging. Therefore, the use of the image quality engine 104 may provide the technician with near instant feedback, as well as instruction on how to better capture the image, thereby enabling the ability for the technician to quickly correct any issues associated with the captured radiological images thereby obviating the need to have the animal undergo multiple radiological image capture sessions. The image quality engine 104 may also apply transformations (e.g., rotations, translations, etc.) and normalized filtering to the received images in order to aid in segmentation and classification as set forth below. Additional discussion of the image quality engine 104 will be described subsequently herein with respect to FIG. 2A.

The system 100 may also include one or more segmentation artificial intelligence engine(s) 106. The one or more segmentation artificial intelligence engine(s) 106 may be trained using one or more segmentation training set(s) 112. For example, one segmentation artificial intelligence engine 106 may be configured to separate out the lung structures of the animal, another segmentation artificial intelligence engine 106 may be configured to separate out the heart structure of the animal, while yet another segmentation artificial intelligence engine 106 may be configured to separate out various skeletal structures of the animal (e.g., the hips, the vertebra, knee joints, ankle joints, etc.). Each of these segmentation artificial intelligence engines 106 may further be characterized by one or more individual segmentation training set(s) 112. For example, segmentation training set #1 112a may be utilized with a first segmentation artificial intelligence engine 106, while another segmentation training set 112n may be utilized for a second segmentation artificial intelligence engine 106. In some instances, a given segmentation artificial intelligence engine 106 may be trained using two (or more) segmentation training sets 112. For example, for a vertebral heart score classification, a given segmentation artificial intelligence engine 106 may require a first segmentation training set 112 for the heart of an animal and a second segmentation training set 112 for the vertebra (or portions thereof) of the animal. These and other variations would be readily apparent to one of ordinary skill given the contents of the present disclosure.

The segmentation training set(s) 112 may include previously segmented radiological images. These previously segmented radiological images may have been previously determined to be accurate by, for example, trained veterinary specialists. For example, when classifying hip dysplasia, the anatomical structure around the pelvis of the animal may be determined to be important. As but another non-limiting example, the lung structures of the animal may be determined to be of importance for other classifications such as pleural effusion, pneumothorax conditions, pulmonary edemas and masses, etc. The previously segmented radiological images may also be characterized dependent upon species or even the breed of the animal. For example, a given segmentation training set 112 may be associated with canine species, while another segmentation training set 112 may be associated with feline species. As but another non-limiting example, a given segmentation training set 112 may be associated with smaller breed canines (e.g., a Chihuahua), while another segmentation training set 112 may be associated with larger breed canines (e.g., a Great Dane). The segmentation training set 112 may also be updated to include ongoing segmented radiological images in order to provide for more robust segmentation. These and other variants would be readily apparent to one of ordinary skill given the contents of the present disclosure.

The segmentation artificial intelligence engine(s) 106 may utilize a deep learning approach (e.g., using region-based convolutional neural networks (R-CNN), single shot multi-box detector (SSD) approaches, and/or You Only Look Once (YOLO) approaches, etc.) and/or machine learning approaches such as support vector machine (SVM) to perform the object classification/segmentation. As discussed supra, one purpose of the segmentation artificial intelligence engine(s) 106 is to segregate various anatomical regions of interest for a particular classification intelligence engine 108. For example, when classifying hip dysplasia conditions in a canine, the segmentation artificial intelligence engine 106 may segregate the pelvis and head of the femur from the remaining skeletal structure of the captured radiographic images. This segmented image may then be fed to the classification artificial intelligence engine 108 associated with classifying hip dysplasia in canines. As but another non-limiting example, when classifying pleural effusion in an animal, the segmentation artificial intelligence engine 106 may separate the lung structures of the animal from other portions of the captured radiological image. The segmented artificial engine 106 may also utilize the separated lung structures of the animal for the purposes of classifying a pneumothorax condition (e.g., a collapsed lung), pulmonary edema, pulmonary masses, etc. Other portions of the anatomy may be segmented dependent upon the classifications being performed (e.g., heart and spine for vertebral heart scale classification, various joints for ligament, patella or stifle effusion classifications, vertebral structure for spondylosis, pelvis for urinary bladder calculi, etc.). These and other anatomic classifications would be readily apparent to one of ordinary skill given the contents of the present disclosure.

The segmentation artificial intelligence engine(s) 106 may decrease the complexity associated with classification of various conditions in an animal. Contrast this approach with prior manually read radiological images in which diagnoses may only be determined based on a holistic view of the entire radiological image. In other words, trained personnel (e.g., veterinary radiologists) would not make diagnoses based on segmented radiological images, rather the entire radiological image would be required in order to make a diagnosis of a particular animal. One drawback of this prior approach is that, for example, veterinary radiologists may be subject to pre-conceived biases. For example, an animal may have been brought into a veterinary clinic due to an owner's concerns about the animal's hips. The veterinary radiologist may find themselves focusing on the animal's pelvic structure and may miss diagnoses for other problems that could also be present in other anatomical structures of the animal. Accordingly, herein lies one salient advantage of the present disclosure, namely the ability for the system 100 to classify the entirety of animal without necessarily being subjected to pre-conceived biases that are inherent with human-made classifications/diagnoses.

Once the radiological images have been segmented by the segmentation artificial intelligence engine(s) 106, these segmented radiological images may be fed to one or more classification artificial intelligence engines 108. Each of the classification artificial intelligence engines 108 may be trained using one or more classification training sets 114. For example, classification artificial intelligence engine #1 108a may be trained using classification training set #1 114a, while classification artificial intelligence engine #2 may be trained with classification training set #1 114a and classification training set #2 114b. Moreover, while not shown in FIG. 1 other classification artificial intelligence engines 108 may be trained using three (or more) classification training sets 114. Moreover, classification artificial intelligence engines 108 may be added subsequent to the establishment of prior classification artificial intelligence engines 108. In such instances, one or more extant classification training sets 114 may be utilized to train the newly added classification artificial intelligence engine 108. Embodiments of the classification artificial engine 108 training procedure will be discussed subsequently herein with respect to FIG. 2B.

The classification artificial intelligence engine(s) 108 may take the form of a deep learning approach such as, for example, a Dense Convolution Network (DenseNet), or may even take a machine learning approach such as, for example and without limitation, those network architectures discussed elsewhere herein. In embodiments that utilize DenseNet, the specific architectures utilized for each of the classification artificial intelligence engines 108 may vary. For example, classification intelligence engine #1 108a may utilize a DenseNet-201 architecture, classification intelligence engine #2 108b may utilize a DenseNet-264 architecture, classification intelligence engine #N 108n may utilize a DenseNet-121 or DenseNet-169 architecture. These and other variants would be readily apparent to one of ordinary skill given the contents of the present disclosure. In some implementations, the architecture for each of the classification artificial intelligence engines 108 may all be the same (or similar) (e.g., DenseNet-201).

The output from each of the classification artificial intelligence engines 108 may further include a confidence level associated with their determined classification. For example, each of the classification artificial intelligence engines 108 may output a classification that is indicative of whether the determined classification is confident that the condition is normal, the condition is likely to be normal, the condition is likely to be abnormal, or the classification of the condition is confident to be abnormal. In some variants, the levels of confidence may be classified under one of three different levels with a classification of one being indicative of a low (or high) confidence that the classification condition is normal (or abnormal), a classification of three being indicative of a high (or low) confidence that the classification condition is abnormal (or normal), and a classification of two being indicative of a confidence level between levels one and three. Moreover, the classification predictions with a high degree of confidence may be added to the classification training sets 114, while classification predictions with a lower degree of confidence may not be added to the classification training sets 114. Moreover, the number value associated the predicted confidence level (e.g., three or four as described previously herein) may be increased in some implementations. For example, the number value associated with the predicted confidence level may vary between one and ten, between one and fifty, or any other suitable number of levels. These and other variants would be readily apparent to one of ordinary skill given the contents of the present disclosure.

One or more of the classification artificial engine(s) 108 may also assist with the identification of species and/or breed of the animal. In some implementations, this identification of species and/or breed for the animal may be compared against metadata associated with the captured image. It has been determined by the assignee of the present application that radiological image metadata incorrectly identifies the breed and/or species of the animal undergoing image capture. For example, the metadata associated with an image captured of a feline may indicate that the associated imaging data has been captured of a canine due to, for example, technician error (e.g., canine may be the default setting and the technician neglects to update the metadata prior to/during/after image capture). In such instances, a classification artificial intelligence engine 108 may determine the discrepancy and may notify, for example, the technician responsible for the entering of the metadata of the error and/or may otherwise correct the metadata contained within captured radiological images. As but another non-limiting example, the metadata associated with a captured image may indicate that the image has been captured a large breed canine, even though the image was captured of a small breed canine. Accordingly, a classification artificial intelligence engine 108 may determine the discrepancy and may notify, for example, the technician responsible for the entering of the metadata of the error and/or may otherwise correct the metadata contained within captured radiological images. These and other variants would be readily apparent to one of ordinary skill given the contents of the present disclosure.

The system 100 may also include an output decision engine 110 which may take as input one or more outputs from the classification artificial intelligence engine(s) 108. For example, an output from classification artificial intelligence engine #1 108a may indicate an abnormal vertebral heart score which may be symptomatic of cardiomegaly or an enlarged heart for the animal. Another output from classification artificial intelligence engine #2 108b may indicate that the metadata associated with the captured images has incorrectly identified the species or breed of the animal that underwent image capture. Accordingly, output decision engine 110 may discount the findings of artificial intelligence engine #1 108a as the parameters associated with the abnormal vertebral heart score may have been misapplied as the output of artificial intelligence engine #1 108a may have been operating under the incorrect assumption that the metadata associated with the captured images was correct. The output decision engine 110 may then re-assess the vertebral heart score given this updated metadata (or may signal to the classification artificial intelligence engine #1 108a to reassess given this updated metadata). In other words, the output decision engine 110 may assess the various outputs from the classification artificial intelligence engines 108 to ensure that their results holistically "make sense."

The system 100 may also include a classification graphical user interface 112 that outputs the result of the output decision engine 110. The output of the classification graphical user interface 112 may indicate the classification of a variety of differing conditions (e.g., pulmonary edema, pulmonary mass(es), pleural effusion, pneumothorax, hip dysplasia, spondylosis, stifle effusion, urinary bladder calculi, etc.). See also FIGS. 3A-3F described subsequently herein. The output of the classification graphical user interface 112 may indicate whether or not the classification is determined to be normal or abnormal for each of the differing conditions and may also indicate a confidence level (e.g., confident condition is normal or confident that the condition is abnormal or that the condition is likely normal or likely abnormal, etc.). The classification graphical user interface 112 may also output (or display) the radiological image and may further include a graphical display of the area of segmentation utilized for the classification of a given condition. For example, when outputting the classification for hip dysplasia, the graphical display may highlight an area around the pelvic structure for the animal. The classification graphical user interface 112 may also display one or more differing radiological images captured for a given animal. The classification graphical user interface 112 may then indicate which one(s) of these differing radiological images captured were utilized for the classification of a given condition. Embodiments of the classification graphical user interface will be described subsequently herein with respect to FIGS. 3A-3F.

The graphical user interface 112 may also display various treatment recommendations that are dependent upon the determination of the output decision engine 110. These various treatment recommendations may be made based upon historical treatment outcomes for a given animal, a given breed of animal, and/or a given species of animal. For example, medication A may be recommended for a canine that has been classified with an abnormal classified condition A and an abnormal classified condition B, yet has a normal classified condition C. Medication B may be recommended for a canine that has been classified with abnormal classified conditions A, B, and C. No medication may be recommended for a canine that has been classified with abnormal condition A, and normal classified conditions B and C. These and other variants would be readily apparent to one of ordinary skill given the contents of the present disclosure. Specific implementation details for the system 100 will now be described in subsequent detail infra.

Exemplary Quality Control Methodologies—

Figure 2A:
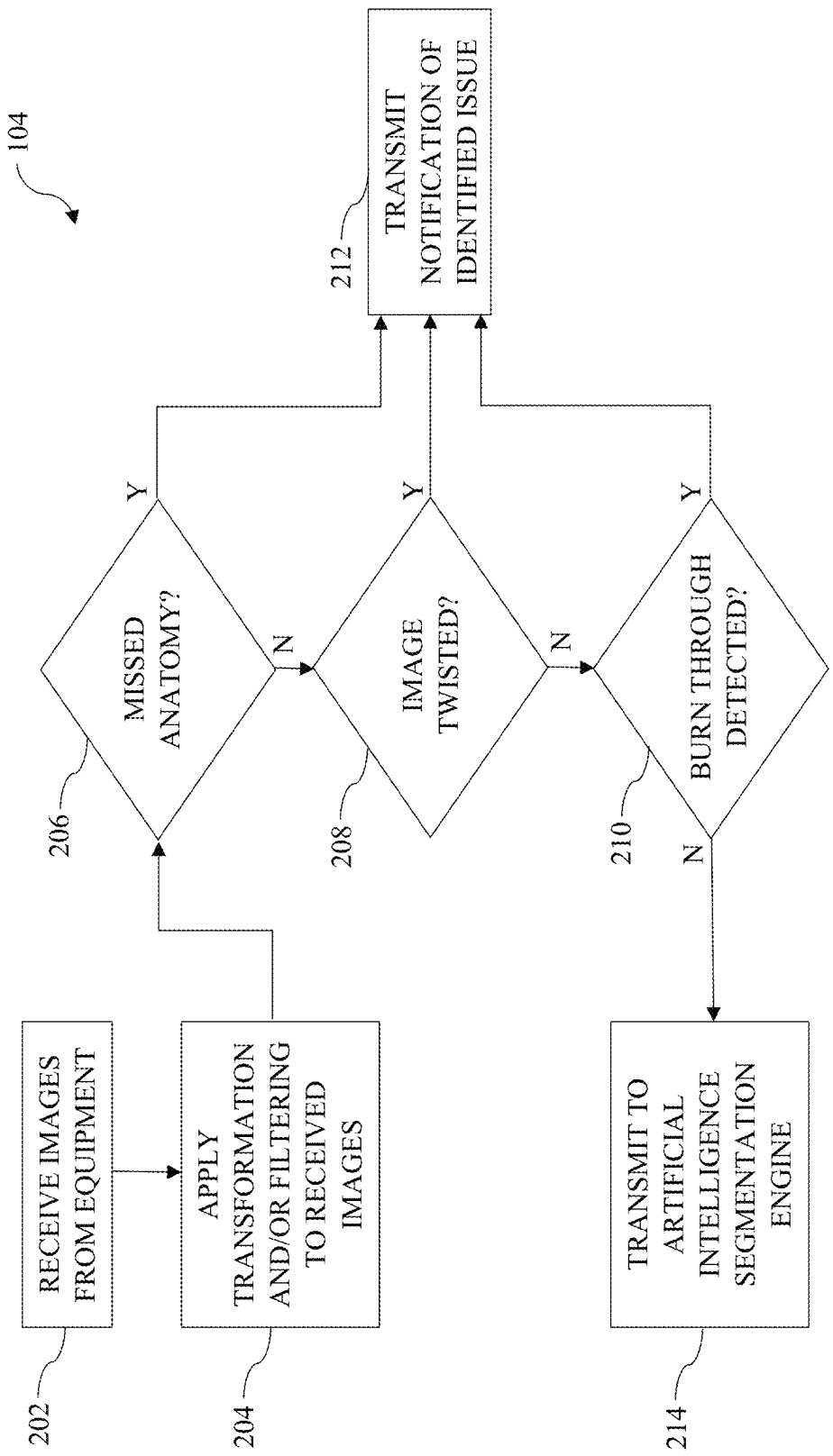
FIG. 2A is a logical flow diagram of one exemplary method for the utilization of a image quality engine, in accordance with the principles of the present disclosure.

Referring now to FIG. 2A, one exemplary quality control methodology for the image quality engine 104 is shown and described in detail. At step 202, the image quality engine 104 receives radiological images captured using the radiological equipment. The received radiological images may take the form of any standard imaging format including, without limitation, Analyze, Neuroimaging Informatics Technology Initiative (Nifti), Minc, and Digital Imaging and Communications in Medicine (Dicom). The images may be received directly from the radiological equipment used to capture the images or may even be received from a storage apparatus (e.g., a hard drive) which stores the images captured by the radiological equipment. In some implementations, the received images include both imaging data (e.g., pixel data) as well as metadata. For example, Dicom imaging data not only contains pixel data, but also includes metadata which includes a description of the medical procedure which led to the formation of the image itself. Common metadata associated with, for example, the Dicom imaging format may include information that describes the procedure for capturing the images (e.g., acquisition protocol and scanning parameters) as well as patient information (e.g., species, breed, age and the like).

At step 204, the received images have transformation operations and/or filtering applied to them. For example, the transformation operations may include rotation operations to ensure consistency with the data contained within, for example, the segmentation training set 112 and/or the classification training set. As but one non-limiting example, the image quality engine 104 may determine the positioning technique utilized for the image capture via, for example, metadata associated with the imaging data or based from machine learning or artificial intelligence approaches. For example, the image quality engine 104 may determine that the received radiological images constitute one of a lateral medial (LM) view, a lateral projection of the body cavities for the animal (e.g., abdomen, thorax), a dorsoventral (DV) view, a ventrodorsal (VD) view, a craniocaudal view, a dorsal palmar (DP) view, or a palmar dorsal (PD) view. Upon determination of the positioning technique utilized for the image capture, the image may be reoriented through rotations and/or translations so as to be consistent with, for example, the training set 112, 114 data. The received images may also undergo normalization techniques that alter the range of pixel intensity values so as to, again, maintain continuity between the received images and the training set 112, 114 data.

The image quality engine 104 may also determine whether essential anatomy has been missed (step 206), whether the animal was moving during image capture (i.e., twisted image) (step 208), and other whether radiological burn through has been detected (step 210). For example, at step 206 the image quality engine 104 may determine that only a partial image of the lung structure has been captured and therefore may optionally discard the image and transmit a notification of the identified issue(s) at step 210. In some implementations, the image may not be discarded and instead will not attempt to classify the missing anatomy using the classification artificial intelligence engine(s) 108. For example, the lung structures may have been captured inadequately, but the other structures of the animal may have been adequately captured. A notification may be transmitted to the DVM or other technician responsible for image capture highlighting that the lung structures have been inadequately captured and the DVM or other technician responsible for image capture may determine that analysis of the lung structures is not needed based on, for example, previous assessment of the animal. These and other variants would be readily apparent to one of ordinary skill given the contents of the present disclosure.

As but another non-limiting example, the image quality engine 104 may detect a twisted radiological image and therefore may optionally discard the image and transmit a notification of the identified issue at step 212. As yet another non-limiting example, the image quality engine 104 may determine that improper energy settings have been applied to the animal for the captured radiological image which may be indicative of under-exposure or over-exposure (e.g., whether more energy needs to be applied to a larger animal or less energy needs to be applied to a smaller animal, etc.) and may optionally discard the image and transmit a notification of the identified issue(s) at step 210.

Herein lies one salient advantage of use of the image quality engine 104, namely, to indicate to the technician or DVM in near-real-time of the inadequacy of the radiological image capture. As discussed elsewhere herein, capturing radiological images of an animal can be stressful for the animal and the near-real-time indication to the technician or DVM may allow for the quick adjustment or re-capture of the radiological image which may minimize the number of procedures and/or the time that the animal has to undergo this otherwise stressful event. In some implementations, this notification may take on any number of forms including a light on a device (e.g., an LED), a communication (e.g., an email or text message to a specified address), an audible indication on a device (e.g., a beep or some other specified tone or sound) etc., which not only identifies that there is a quality control issue with the captured radiological image, but may also indicate what the identified issue is (e.g., missed anatomy and what specific portion of the anatomy has been missed, animal movement during image capture, and/or the detection of improper radiological image capture settings). Upon successful recapture of a radiological image of sufficient quality, the captured radiological image is transmitted to the artificial intelligence segmentation engine(s) 106 at step 214. In some implementations, the image quality engine 104 may also indicate to the technician or DVM successful image capture though a light on a device (e.g., an LED), a communication (e.g., an email or text message to a specified address), an audible indication on a device (e.g., a beep or some other specified tone or sound) etc.

Figure 2B:
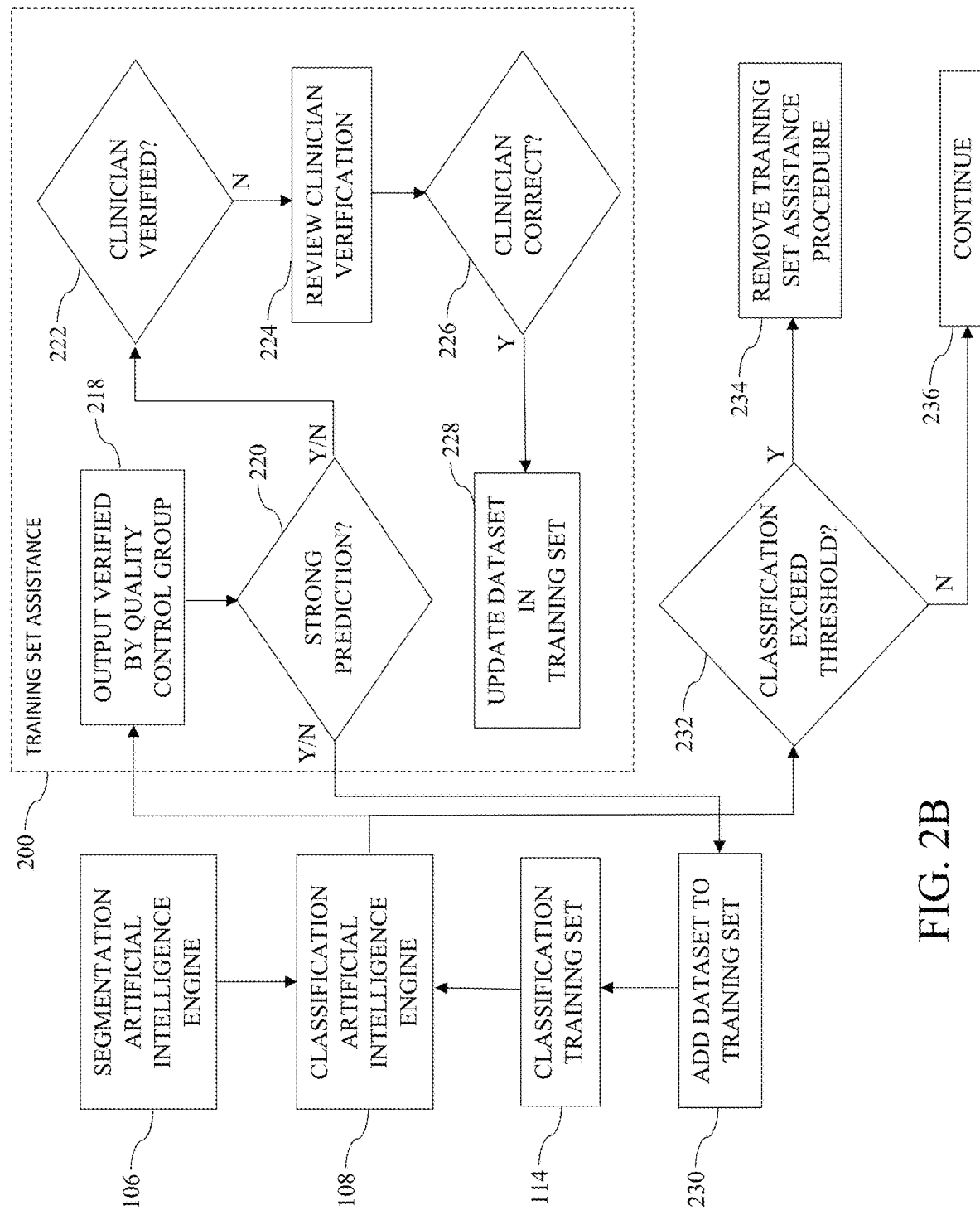
FIG. 2B is a logical flow diagram of one exemplary method for the training of a classification artificial intelligence engine, in accordance with the principles of the present disclosure.

Referring now to FIG. 2B, a logical flow diagram of one exemplary method for the training of a classification artificial intelligence engine 108 is shown and described in detail. Specifically, once the segmentation artificial intelligence engine(s) 106 has transmitted the segmented radiological images to the respective classification artificial intelligence(s) 108, a training set assistance procedure 200 is implemented. The training set assistance procedure 200 first verifies the output of the classification by using a quality control group at step 218. For example, a trained human may verify the output of the classification (e.g., confident abnormal, likely abnormal, likely normal, and confident normal). If the trained human disagrees with the output of the classification artificial intelligence engine(s) 108, the trained human may update the classification (e.g., from likely abnormal to confident abnormal, as but one non-limiting example). Conversely, if the trained human agrees with the output of the classification artificial intelligence engine 108, the outputted classification is not updated. Regardless of whether or not the trained human agrees or disagrees with the output of the classification artificial intelligence engine 108, the results may then be passed along to, for example, a trained DVM or supervisor. The trained DVM or supervisor may then update the classification, if necessary, prior to forwarding on the results to the clinician who captured the radiological image.

If a strong prediction (e.g., confident abnormal or confident normal) has been verified by the DVM or supervisor, the segmented radiological image may be added to the classification training set 114 at step 230. In some implementations, the segmented radiological image may be added to the classification training set 114 at step 230, regardless of the confidence of the prediction. Regardless of whether or not the prediction (classification) from the classification artificial intelligence engine 108 is indicative of a strong classification, the results of the quality control group are forwarded on to the requesting clinician at step 222, where the results of the classification are verified by the clinician. If the requesting clinician disagrees with the classification at step 222, the requesting clinician's findings are forwarded back to the quality control group for re-review at step 224. In some implementations, the requesting clinician will forward their findings back to the quality control group whether or not they disagree with the classification. Upon re-review, the quality control group (e.g., the trained human and/or the DVM or supervisor) will determine whether or not they agree with the requesting clinician's findings at step 226. In some implementations, the results of the re-review are not forwarded back to the requesting clinician. One potential reason for not forwarding back the clinician verification is to encourage cooperation from the requesting clinicians in the training set assistance procedure.

If the re-review of the clinician's disagreement with the classification results are verified by the quality control group, the dataset may be removed (or otherwise updated) from the training set at step 228. In some implementations, so long as the dataset was previously added to the training set as a result of a strong prediction classification, the dataset may be updated or removed. Once the classification results exceed a threshold value at step 232, the training set assistance procedure may be removed from the process at step 234. Upon removal of the training set assistance procedure, strong predictions output by the classification artificial intelligence engine 108 may continue to be added to the classification training set 114. If however, the classification results do not exceed the threshold value at step 232, continued use of the quality control group and the training set assistance procedure 200 is utilized.

The training set assistance procedure 200 may be performed individually for each of the classification artificial intelligence engines 108. For example, the classification results for classification artificial intelligence engine #1 108*a* may exceed the classification threshold and therefore the training set assistance procedure 200 for classification artificial intelligence engine #1 108*a* may be turned off. Conversely, the classification results for classification artificial intelligence engine #2 108*b* may not exceed the classification threshold and therefore the training set assistance procedure 200 for classification artificial intelligence engine #2 108*b* may continue to be utilized. Accordingly, the exemplary method for the training of a classification artificial intelligence engine 108 is considered a robust procedure that will encourage its widespread adoption throughout, for example, the veterinary community. Moreover, the classification results threshold may be chosen dependent upon, for example, the desirability of the widespread adoption of the system 100. In some implementations, the classification results threshold may be set to 95%, although lower or higher classification results may be chosen in accordance with, for example, the goals established by the operator of the system 100.

Exemplary Classification Graphical User Interfaces—

Figure 3A:
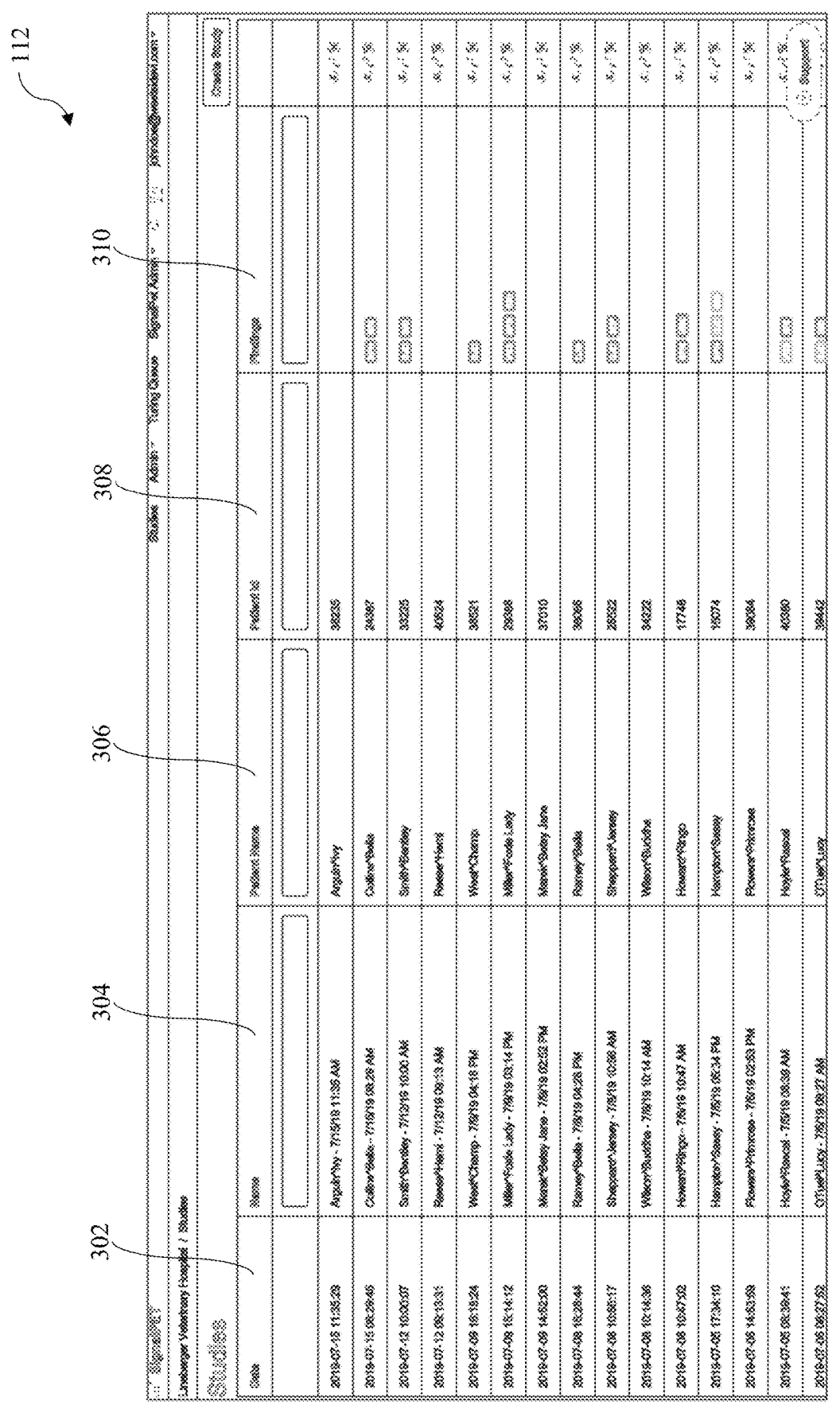
Figure 3B:
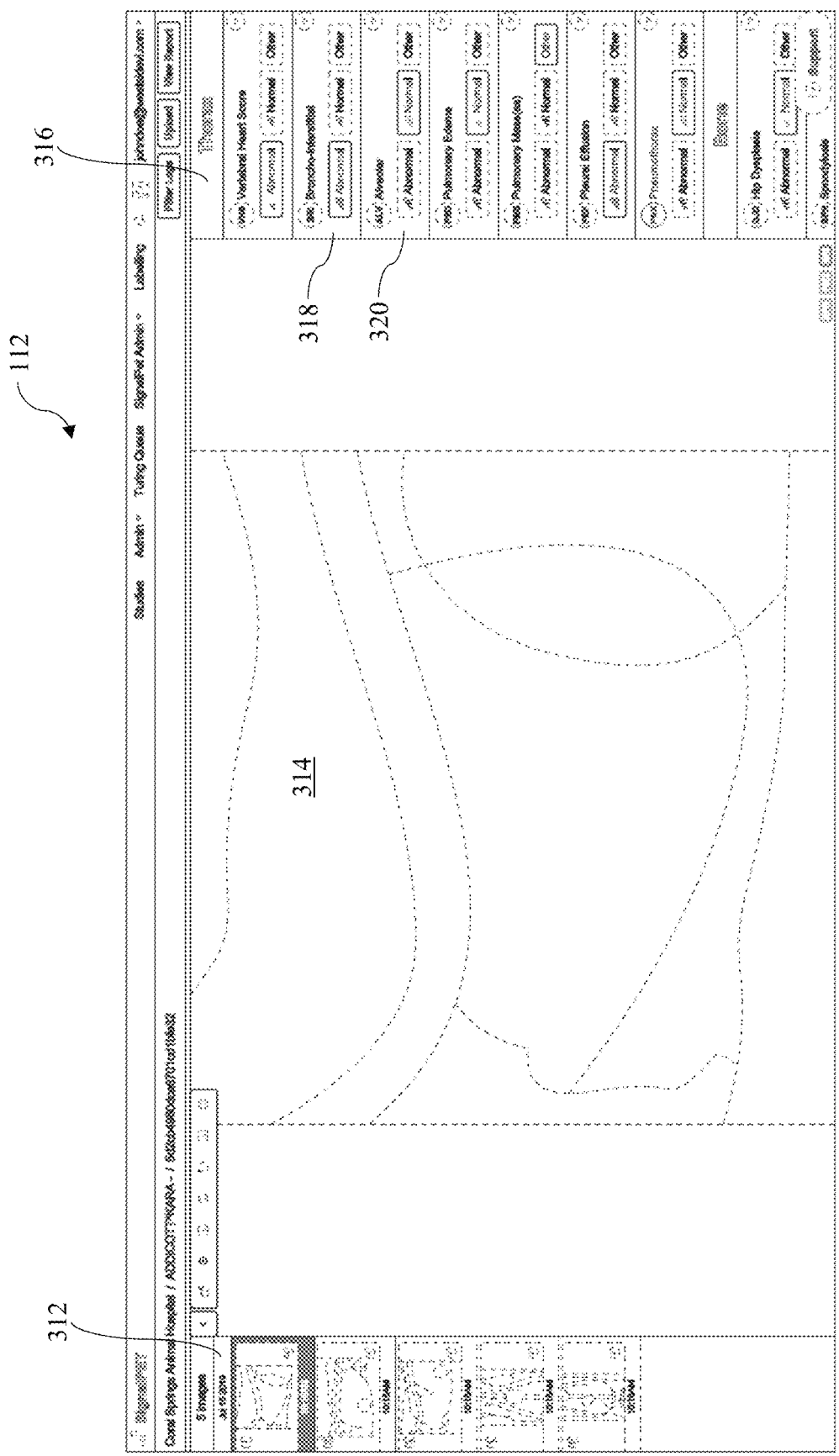
FIG. 3B is a second exemplary graphical user interface display indicative of a classification for a given animal, in accordance with the principles of the present disclosure.

Referring now to FIGS. 3A-3F, various classification graphical user interface displays 112 are shown and described in detail. FIG. 3A illustrates a graphical user interface display 112 that includes a plurality of columns. For example, column 302 may include the date/time of image capture, column 304 may the name(s) of the animals owner, column 306 may include the name of the animal that underwent imaging, column 308 may include the patient's identification number, and column 310 may include a summary of classified maladies. In some implementations, one or more of the aforementioned columns may be removed from the graphical user interface display 110. In other implementations, one or more additional columns may be added in addition to (or alternatively than) the columns shown in FIG. 3A. For example, instead of containing a single classification column 310, two or more classification columns may be displayed on the graphical user interface display 110. One classification column 310 may indicate abnormal classification(s), while another classification column 310 may indicate normal classification(s). These and other variants would be readily apparent to one of ordinary skill given the contents of the present disclosure.

The classification column 310 may include a colored box along with initials. The initials may be representative of an identified classification, while the color may be indicative of the confidence level of the classification and may also be indicative of whether or not the classification is normal or abnormal. For example, the red color may be indicative of a confident abnormal classification, while the orange color may be indicative of a likely abnormal classification. Additional colors may be utilized for likely normal and confident normal classifications. Other color schemes may be utilized in some implementations. Additionally, while initials for various classifications are illustrated in FIG. 3A, in some implementation's full words or even numbers (or symbols) may be utilized in addition to, or alternatively than, the aforementioned initials.

FIG. 3B illustrates another exemplary graphical user interface display 112. On the left-hand side of the display 112, column 312 is shown with five (5) different images. Each of these images have been taken of the same animal. In some implementations, more (six (6) or more) or less (four (4) or fewer) images may have been captured. The image highlighted in blue is the same as the larger image 314 in the center of the display. In the right-hand column 316, various classifications are displayed along with an indication of whether the classification is normal or abnormal. In addition to the classification of normal or abnormal, a confidence indicator is associated with the normal or abnormal rating. For example, in the classification for condition 318, coloring (e.g., red) is indicative of an abnormal classification. Next to the abnormal classification may be a series of four columns with each column having a different height. As can be seen in condition 318, all four columns are highlighted in red which is indicative of a confident abnormal classification. If only two of the four columns were colored, this would be indicative of a likely abnormal classification. For condition 320, the coloring (e.g., green) is indicative of a normal classification, while the number of green columns is indicative of the confidence level of the classification. For example, four colored columns are indicative of "strong" classification, while less colored columns (e.g., two) would be indicative of a less confident classification, etc.

Figure 3C:
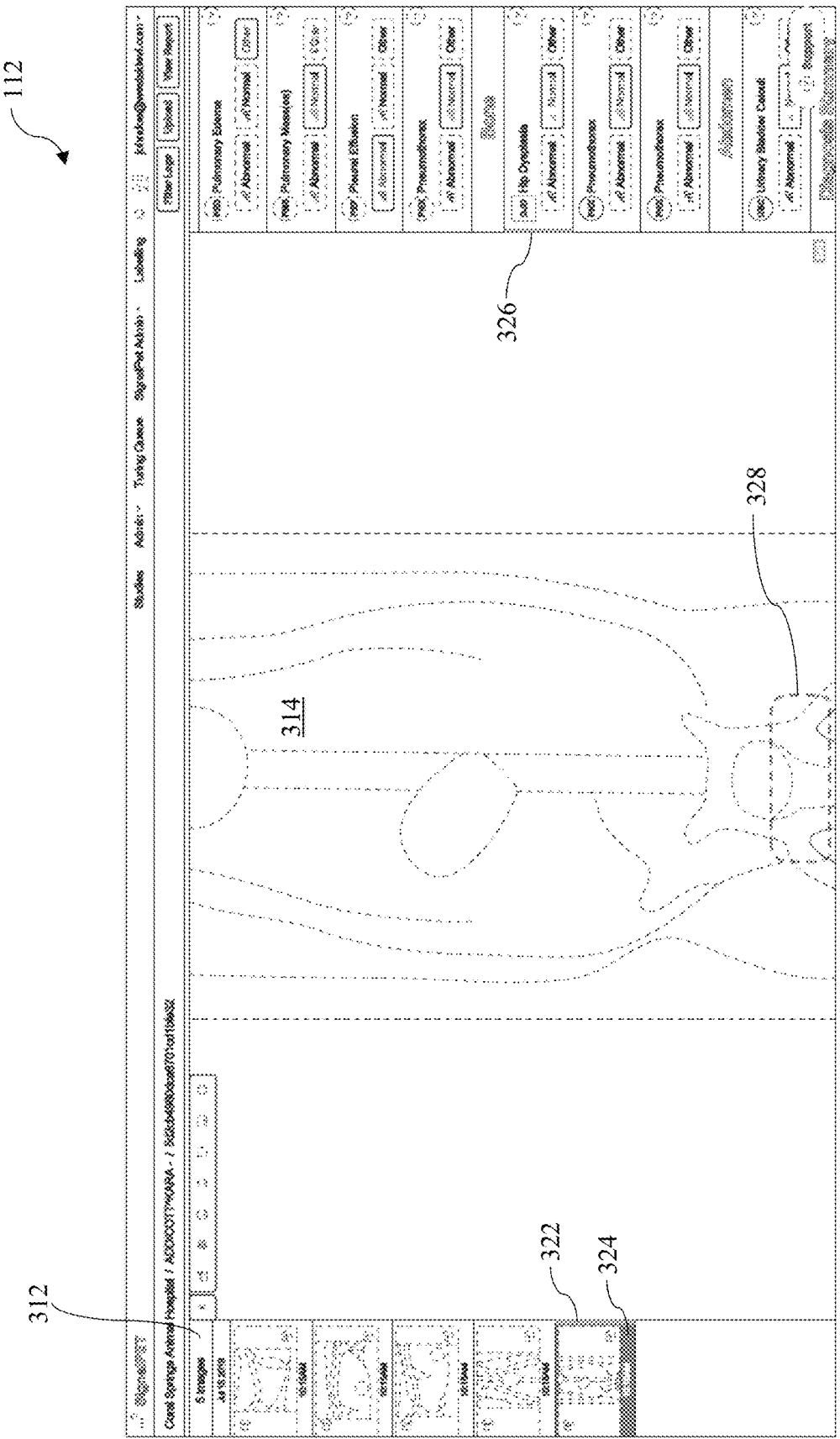
FIG. 3C is a third exemplary graphical user interface display indicative of a classification for a given animal, in accordance with the principles of the present disclosure.

FIG. 3C illustrates yet another exemplary graphical user interface display 112. Similar to FIG. 3B, on the left-hand side of the display 112, column 312 is shown with five (5) different images. Each of these images have been taken of the same animal. Similar to that shown in FIG. 3B, the image 324 highlighted in blue is the same as the larger image 314 in the center of the display. In the right-hand column, various classifications are displayed along with an indication of whether the classification is normal or abnormal. As can be seen in condition 326 (hip dysplasia), two of the four columns are highlighted in green which is indicative of a likely normal classification. A segmentation outline 328 is overlaid on the center image 314 which is indicative of the segmented portion of the radiological image used for the condition 326 classification. The condition 326 has been selected as indicated by the green highlighting on the left-hand side of the condition. Similarly, the left-hand column 312 includes green highlighting 322. The green highlighting 322 indicates that this is the only image of the five (5) total shown used for the classification for hip dysplasia. Green highlighting is used for both the condition 326 as well as the image 322 as this condition is classified as normal. However, if this condition were considered abnormal, the highlighting would be red. While color and positioning of the various aspects within the graphical user interface display 112 of FIG. 3C is shown, it would be recognized by one of ordinary skill given the contents of the present disclosure that the coloring and/or positioning scheme illustrated could be readily modified in alternative variants.

Figure 3D:
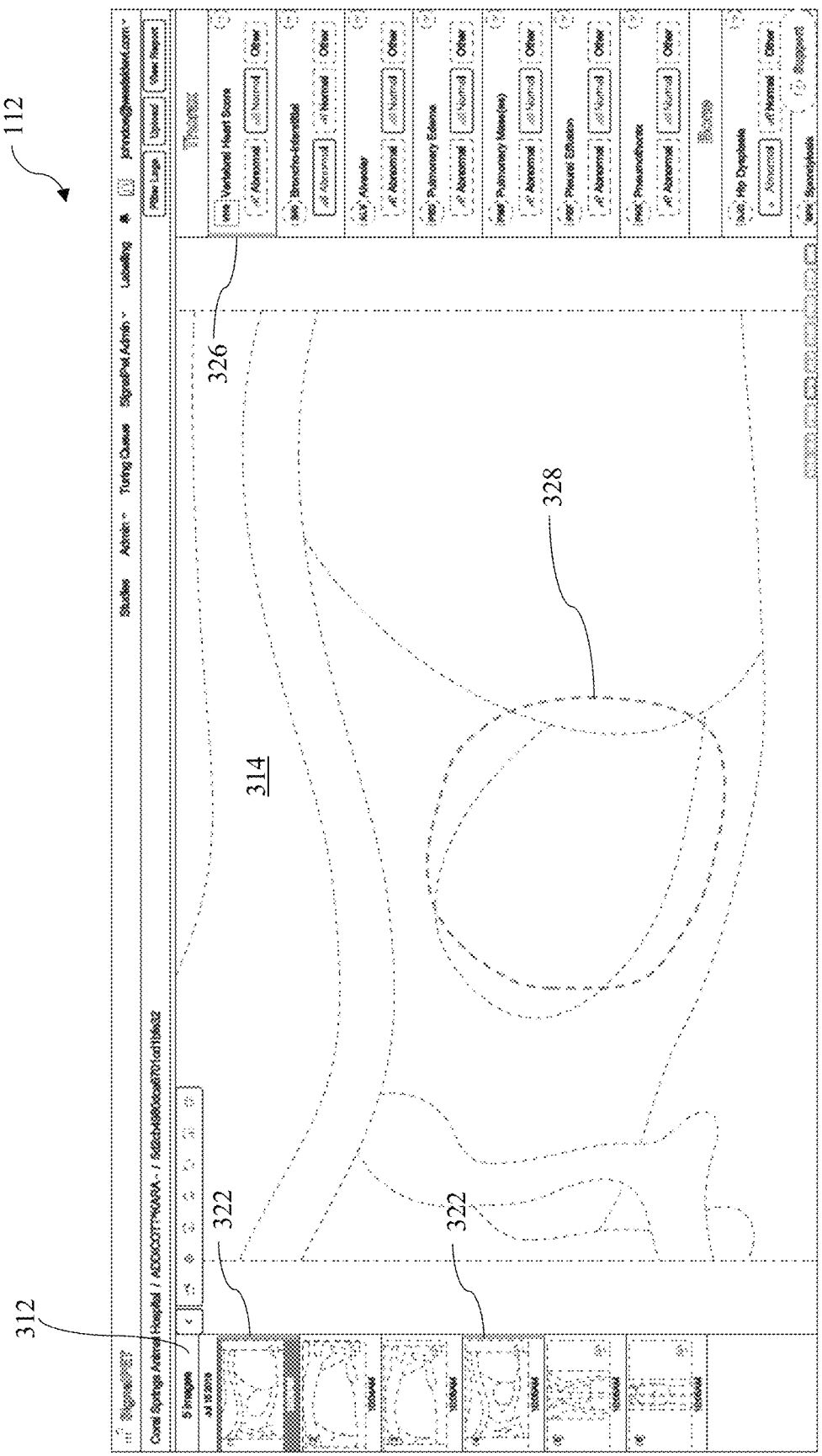
FIG. 3D is a fourth exemplary graphical user interface display indicative of a classification for a given animal, in accordance with the principles of the present disclosure.

FIG. 3D illustrates yet another exemplary graphical user interface display 112. The display 112 shown in FIG. 3D is similar to that shown in FIG. 3C; however, in the embodiment of FIG. 3D, the condition 326 selected is vertebral heart score. As can be seen in the left-hand column 312 two (2) (of the six (6) total) images contain green highlighting 322. The reasoning that two (2) of these images include green highlighting is because these two (2) images were utilized in classifying the vertebral heart score for the animal. Additionally, the segmentation outline 328 is now around the heart of the animal indicating that this portion of the image was segmented out prior to being classified.

Figure 3E:
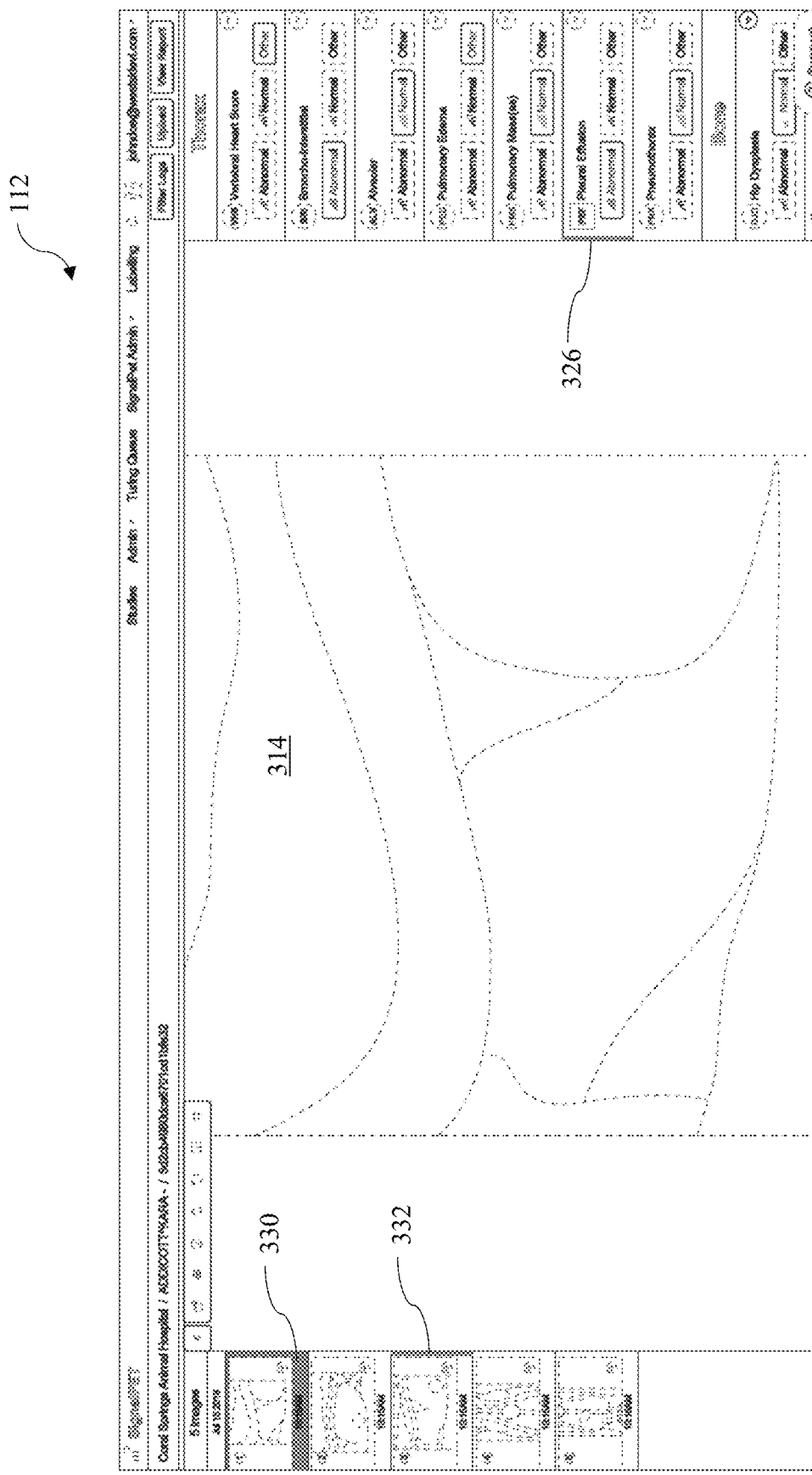
FIG. 3E is a fifth exemplary graphical user interface display indicative of a classification for a given animal, in accordance with the principles of the present disclosure.

FIG. 3E illustrates yet another exemplary graphical user interface display 112. In this display 112, the condition 326 pleural effusion has been selected. The center image 314 is the image 330 that is currently selected. However, because the condition 326 classification is based on an image 332 that has not been selected, there is no segmentation outline located within the center image 314 of FIG. 3E. However, if the image 332 was selected, there would be a segmentation outline (here the lung structure) that would be indicative of the segmented portion of the radiological image.

Figure 3F:
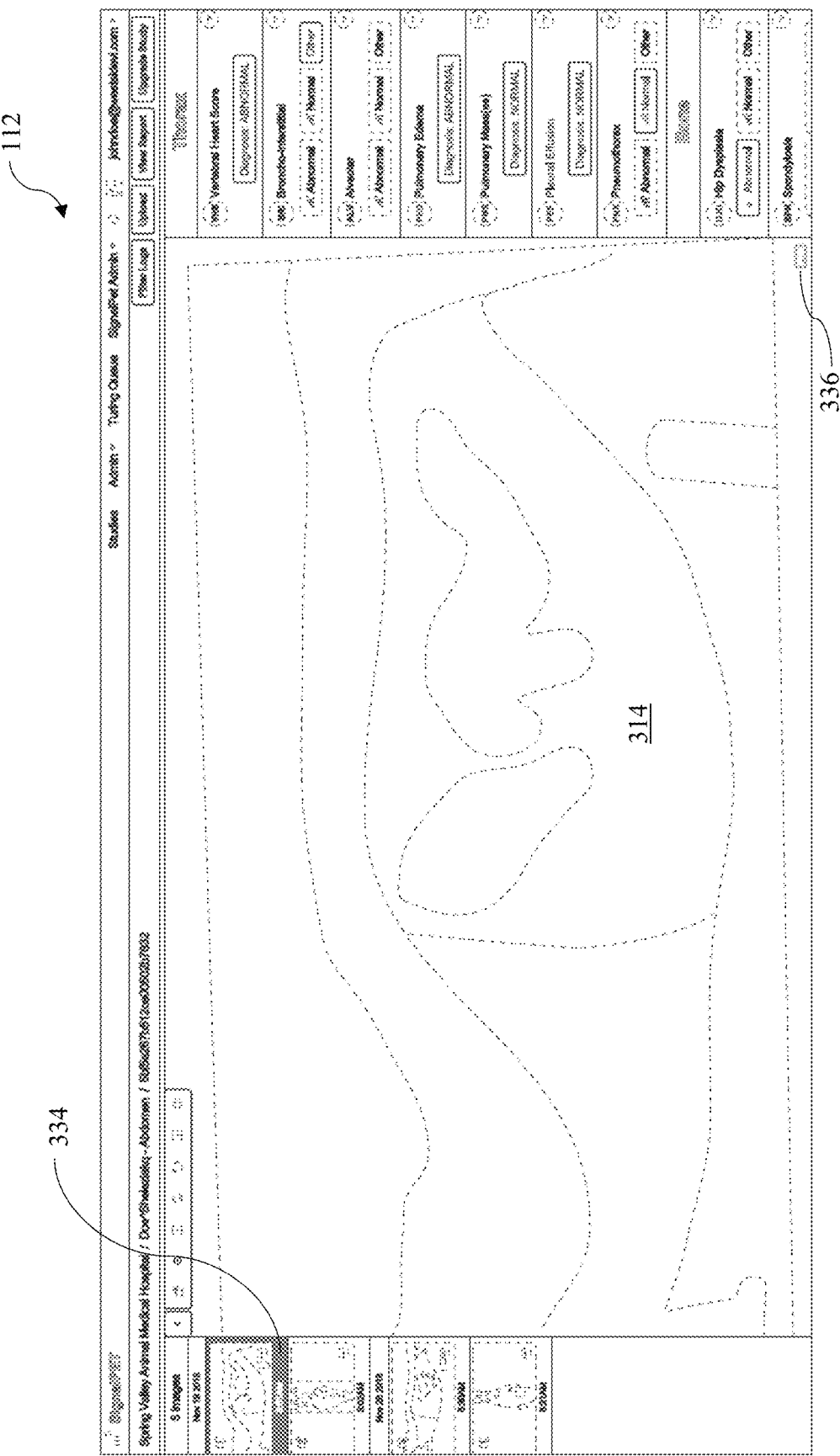
FIG. 3F is a sixth exemplary graphical user interface display indicative of the types of classifications for a given image, in accordance with the principles of the present disclosure.

FIG. 3F illustrates yet another exemplary graphical user interface display 112. In this display 112, the image 334 highlighted in blue is the same as the image 314 in the center of the display. The selected image 334 also identifies what classifications 336 have been determined based on the selected image 334. In this example display 112, only a single classification (pneumothorax) has been determined based on this image, although it would be readily appreciated that a given image may be utilized for two (or more) classifications. These and other variants would be readily apparent to one of ordinary skill given the contents of the present disclosure.

Figure 3G:
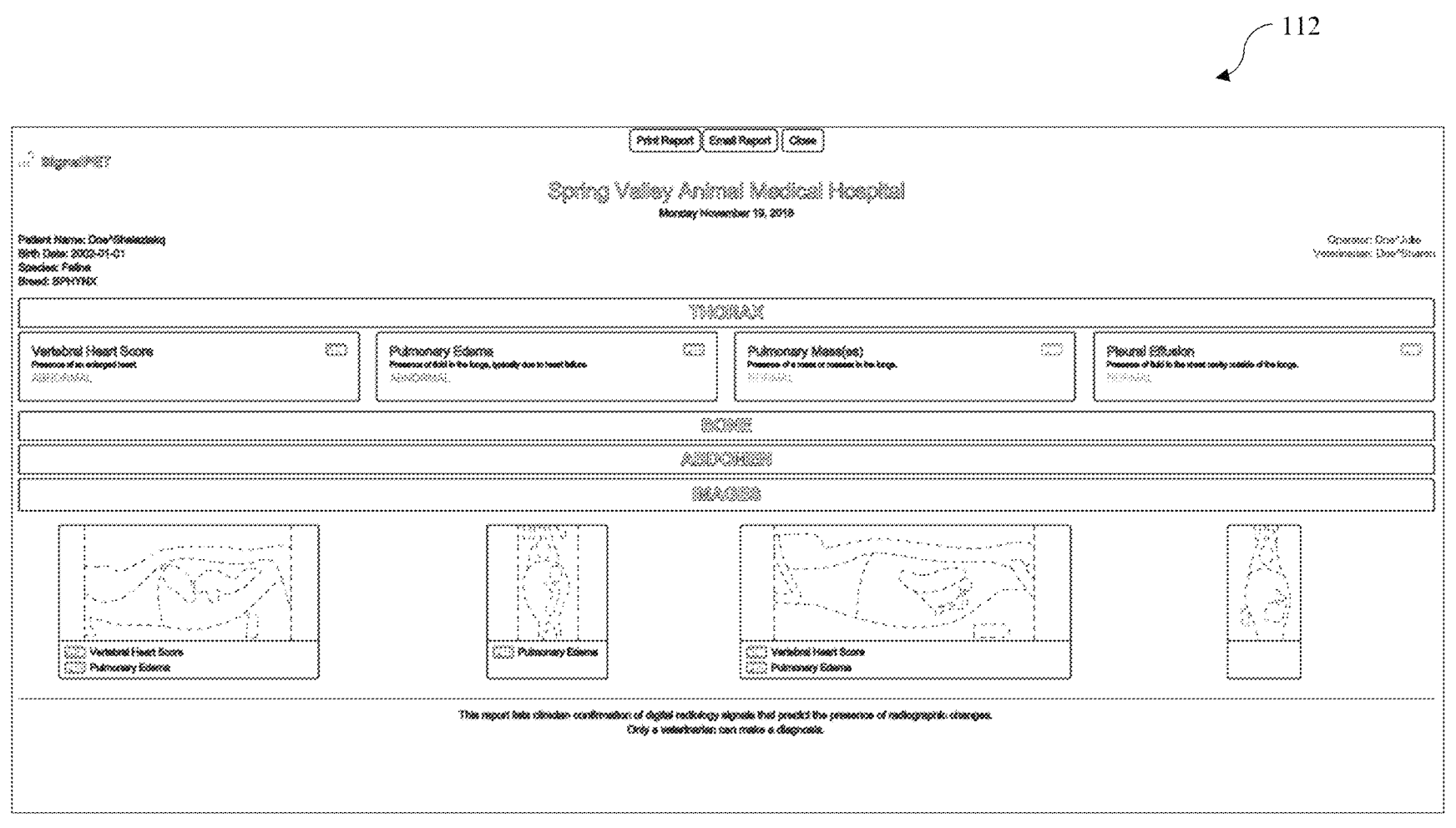

FIG. 3G illustrates yet another exemplary graphical user interface display 112. In this display 112, a summary of the findings of the classification artificial intelligence engine(s) is displayed to the user. The display 112 includes the name of the patient as well as the name of the treating veterinary facility. The display also includes a summary of the various normal/abnormal findings made using the system 100. These normal/abnormal findings may be broken down by type (e.g., thorax, bone, abdomen, etc.). Additionally, representative images may be included which were used in these normal/abnormal classifications. The display 112 may also include recommended treatment options for the patient in some implementations. These recommended treatment options may be updated over time as various outcomes for the recommended treatment options become known. In other words, these recommended treatment options may be updated to include information as to treatment success as a function of various other identified normal/abnormal criteria. While a particular display 112 is shown, it would be readily apparent to one of ordinary skill that the display 112 would vary from animal-to-animal.

It will be recognized that while certain aspects of the present disclosure are described in terms of specific design examples, these descriptions are only illustrative of the broader methods of the disclosure and may be modified as required by the particular design. Certain steps may be rendered unnecessary or optional under certain circumstances. Additionally, certain steps or functionality may be added to the disclosed embodiments, or the order of performance of two or more steps permuted. All such variations are considered to be encompassed within the present disclosure described and claimed herein.

While the above detailed description has shown, described, and pointed out novel features of the present disclosure as applied to various embodiments, it will be understood that various omissions, substitutions, and changes in the form and details of the device or process illustrated may be made by those skilled in the art without departing from the principles of the present disclosure. The foregoing description is of the best mode presently contemplated of carrying out the present disclosure. This description is in no way meant to be limiting, but rather should be taken as illustrative of the general principles of the present disclosure. The scope of the present disclosure should be determined with reference to the claims.

What is claimed is:

1. A method for identification of various physiological conditions of an animal using machine learning, the method comprising:

receiving one or more radiographic images captured of the animal;

receiving non-imaging biological data for the animal;

segmenting the received one or more radiographic images captured of the animal using one or more segmentation artificial intelligence engines to create a set of segmented radiographic images, each of the set of segmented radiographic images corresponding to a specific anatomical area within the animal, the segmenting of the received one or more radiographic images captured of the animal comprises segregating a given organ and/or a given skeletal structure from remaining portions of the received one or more radiographic images captured of the animal;

providing the set of segmented radiographic images to respective ones of a plurality of classification artificial intelligence engines;

providing the received non-imaging biological data for the animal to one or more of the plurality of classification artificial intelligence engines;

outputting results from the plurality of classification artificial intelligence engines for the set of segmented radiographic images and the non-imaging biological data to an output decision engine, the outputting of the results from the plurality of classification artificial intelligence engines comprises outputting either a normal condition or an abnormal condition along with a confidence level associated with the normal condition or the abnormal condition;

providing recommended courses of action, using the output decision engine, based on the output results from the plurality of classification artificial intelligence engines;

analyzing metadata associated with the received one or more radiographic images captured of the animal;

comparing the analyzed metadata with the output results in order to determine misapplied parameters associated with a subset of the plurality of classification artificial intelligence engines; and selectively discarding the output results associated with the misapplied parameters.

2. The method of claim 1, wherein the providing of the recommended courses of action comprises providing further diagnostics that may be needed to treat the animal.

3. The method of claim 1, wherein the providing of the recommended courses of action comprises providing treatment recommendations for the animal.

4. The method of claim 3, wherein the providing of the treatment recommendations for the animal are based on using one or more of historical treatment outcomes for the animal, historical treatment outcomes for a given breed of the animal, and/or historical treatment outcomes for a given species of the animal.

5. A non-transitory computer-readable storage apparatus comprising a plurality off instructions, that when executed by a processor apparatus, are configured to:

receive one or more radiographic images captured of an animal;

receive non-imaging biological data for the animal;

segment the received one or more radiographic images captured of the animal via use of one or more segmentation artificial intelligence engines to create a set of segmented radiographic images, each of the set of segmented radiographic images corresponding to a specific anatomical area within the animal;

provide the set of segmented radiographic images to respective ones of a plurality of classification artificial intelligence engines;

provide the received non-imaging biological data for the animal to one or more of the plurality of classification artificial intelligence engines;

output results from the plurality of classification artificial intelligence engines for the set of segmented radiographic images and the non-imaging biological data to an output decision engine;

provide recommended courses of action, via use of the output decision engine, based on the output results from the plurality of classification artificial intelligence engines;

output the recommended courses of action from the output decision engine to a graphical user interface (GUI), the GUI including the one or more radiographic images, a centralized radiographic image from the one or more radiographic images, and a plurality of classifications;

receive a first selection for one of the plurality of classifications; and highlight one or more of the one or more radiographic images that were utilized in assessing the first selection of the plurality of classifications.

6. The non-transitory computer-readable storage apparatus of claim 5, wherein the plurality of instructions, when executed by the processor apparatus, are further configured to:

cause display of a first segmentation outline within the centralized radiographic image, the first segmentation outline representing a first anatomical area of interest utilized in the assessment of the first selection for the one of the plurality of classifications.

7. The non-transitory computer-readable storage apparatus of claim 6, wherein the plurality of instructions, when executed by the processor apparatus, are further configured to:

analyze metadata associated with the received one or more radiographic images captured of the animal;

compare the analyzed metadata with the output results in order to determine misapplied parameters associated with a subset of the plurality of classification artificial intelligence engines; and selectively discard the output results associated with the misapplied parameters.

8. The non-transitory computer-readable storage apparatus of claim 6, wherein the provision of the recommended courses of action comprises provision of one or more diagnostics that may be needed to treat the animal.

9. The non-transitory computer-readable storage apparatus of claim 8, wherein the provision of the recommended courses of action comprises provision of one or more treatment recommendations for the animal.

* * * * *